(12) United States Patent
Weinberg et al.

(10) Patent No.: US 6,539,259 B1
(45) Date of Patent: Mar. 25, 2003

(54) SYSTEM AND METHOD OF AUTOMATICALLY ADJUSTING SENSITIVITY IN AN IMPLANTABLE CARDIAC STIMULATION DEVICE

(75) Inventors: Lisa P. Weinberg, Moorpark, CA (US); Gene A. Bornzin, Simi Valley, CA (US); Kelly H. McClure, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/354,244

(22) Filed: Jul. 15, 1999

(51) Int. Cl.$^7$ .................................................. A61N 1/18
(52) U.S. Cl. ........................................................ 607/9
(58) Field of Search ...................... 607/9, 28; 600/509

(56) References Cited

U.S. PATENT DOCUMENTS

| | | | |
|---|---|---|---|
| 4,708,144 A | 11/1987 | Hamilton et al. | 128/419 |
| 4,766,902 A | 8/1988 | Schroeppel | 128/419 |
| 4,768,511 A | 9/1988 | DeCote, Jr. | 128/419 |
| 5,269,300 A | 12/1993 | Kelly et al. | 607/4 |
| 5,564,430 A | 10/1996 | Jacobson et al. | 128/697 |
| 5,913,880 A | 6/1999 | Vonk | 607/27 |

*Primary Examiner*—Mark Bockelman (57) ABSTRACT

A system and method are disclosed for automatically adjusting the sense amplifier sensitivity based on the sensing threshold of the undesired signals (i.e., far-field signals or undesired near-field signals). Specifically, R-wave sensitivity is based on the peak amplitude of the T-waves. Since the relationship between R-waves and T-waves is so repeatable, high confidence is achieved in setting the sensitivity above the T-wave sensing threshold. For atrial sensing, P-wave sensitivity is based on the sensing threshold of R-waves and/or T-waves, whichever is larger. Several embodiments are disclosed for determining the threshold for sensing the undesired signals, such as, double sensing until single sensing occurs, or otherwise detecting the peak amplitude of two or more cardiac signals. Additional error checking may be employed, particularly for atrial sensitivity adjustment, to ensure proper detection of the sensing threshold for the undesired signals in patients with heart block: including analysis of the respective amplitude, cardiac signal duration, and time relationships to appropriately classify the cardiac signals.

27 Claims, 9 Drawing Sheets

SYSTEM AND METHOD OF AUTOMATICALLY ADJUSTING SENSITIVITY IN AN IMPLANTABLE CARDIAC STIMULATION DEVICE

FIELD OF THE INVENTION

The present invention is directed towards an implantable stimulation device, such as a cardiac pacemaker or an implantable cardioverter-defibrillator device, which has a system that automatically and reliably adjusts its sensitivity for sensing cardiac signals and for reliably discriminating between P-waves, R-waves and T-waves, even in the presence of noise and complete heart block.

BACKGROUND OF THE INVENTION

Every modern implantable stimulation device includes sensing capability, whether in one or two chambers of the heart. Typically, sensing of the low amplitude cardiac signals is achieved by a pre-amplifier and a comparator which detects if a predetermined threshold have been exceeded. The "sensitivity" is generally thought of as a measure of the level, in millivolts, in which a cardiac signal must exceed in order to be detected by the sensing circuitry. If the sensitivity is too low (i.e., too insensitive), then some cardiac events will not be detected. If the sensitivity is too high, then erroneous sensing of noise or undesired cardiac signals may result (e.g., the double sensing of T-waves may occur, noise may be mistaken for P-waves, and far-field R-waves may be mistaken as P-waves, etc.).

Systems for automatic sensitivity control in an implantable stimulation device have long been plagued by the inability to reliably detect the low amplitude P-waves signals (typically about 4 mV) in the presence of noise and myopotentials, and by the inability to discriminate P-waves and R-waves from T-waves. Although a physician may be able to readjust the sensitivity of the device, many patients are unable to see their physicians frequently enough. This problem is compounded when several other factors may also affect the device's sensitivity as a function of time, such as fibrotic tissue growth, drugs, dislodgment, arrhythmias, changes due to defibrillation shock, etc. Thus, it is desirable to have a system that can automatically and reliably adapt itself as the patient's needs change.

Many schemes have been attempted which require additional sensing amplifiers and hardware, which in turn require more real estate on the IC's and more current drain. For example, Hamilton et al. (U.S. Pat. No. 4,708,144) discloses a system for measuring a peak R-wave and deriving a long term average to determine the gain setting and threshold of the amplifier. This configuration requires a conventional amplifier and a comparator, in addition to, an attenuator, a filter, an A/D converter, an absolute value circuit and a peak detector.

Decote, Jr. (U.S. Pat. No. 4,768,411) discloses a dual comparator system, having two different thresholds but coupled to the same input, which simultaneously adjusts each threshold until one comparator senses the cardiac signal and one does not. In addition to a conventional amplifier and comparator, this system requires a precision signal rectifier, a D/A converter, a voltage divider, and a second comparator. The reference by Schroeppel (U.S. Pat. No. 4,766,902) teaches a similar approach albeit with less specificity.

Baker, Jr. et al. (U.S. Pat. No. 4,903,699) discloses an even more complicated scheme using a quad-comparator system for separately determining sensing threshold and amplifier gain. This system requires an automatic gain control circuit, three amplifiers, and four comparators.

It is also known that low amplitude ventricular fibrillation (VF) can go undetected if the sensitivity level (in mV) is set for normal bradycardia activity. If the sensitivity level is set too high (i.e., too sensitive), however, then double sensing of T-waves can result in erroneously classifying a rhythm as VF. Also, it is known that, post defibrillation shock, the current of injury T-wave can be higher in amplitude than R-waves. The Grevis et al. reference (U.S. Pat. No. 4,940,054) discloses a system for setting the sensing circuitry to any one of a multiple sensitivities depending on the type of rhythm detected, or expected, based on the present therapy.

Different ones of the electrode configurations have proven more useful than others for sensing certain cardiac events. Briefly, the benefits of bipolar leads are well known: for example, capture detection is superior when used with bipolar electrodes. Also, it is well known that bipolar stimulation can eliminate pectoral stimulation; bipolar sensing can eliminate sensing of noise and EMI. In some instances, unipolar sensing may provide a larger cardiac signal based on the vector; and unipolar stimulation may avoid diaphragm stimulation in some patients. Implanting bipolar leads enables complete programmable polarity. Thus, if the patient needs a different electrode configuration to avoid a pacing or sensing problem, or if a wire fractures, the physician can reprogram the electrode configuration to an alternative pair of operable electrodes. The need to change sensing electrode configurations provides yet another reason for automatically determining a new sensitivity setting, and this need is magnified if the implanted device can perform this reprogramming automatically based on predefined criteria (e.g., an improper lead impedance, a change in the rhythm, etc).

The problem of accurately automatically sensing P-waves and R-waves is even more pronounced when using an "A-V combipolar" electrode configuration, that is, an electrode configuration in which the stimulation device senses cardiac signals between an atrial tip electrode and a ventricular tip electrode, and stimulates each chamber in a unipolar fashion from the respective electrode to the housing (i.e., typically referred to as the case electrode). For a more complete description of combipolar systems, see U.S. Pat. No. 5,522,855 (Hognelid), which reference is incorporated herein by reference. When such electrodes are implanted, various electrode sensing configurations are possible, e.g., atrial unipolar (Atip-case); ventricular unipolar (Vtip-case); atrial-ventricular combipolar (Atip-Vtip); ventricular unipolar ring (Vring-to-case) or atrial unipolar ring (Aring-to-case).

Regardless of the cardiac event being sensed, however, and regardless of the electrode configuration being used, there is a need for the implantable device to be able to readily and reliably distinguish between P-waves, R-waves and T-waves. This is because the implantable device, if it is to perform its intended function, must know when an atrial depolarization occurs (P-wave), and when a ventricular depolarization occurs (R-wave), and it must not be fooled by falsely sensing a T-wave or noise as a P-wave or R-wave.

For example, it is of critical importance that the device be capable of recognizing the occurrence of certain atrial arrhythmias based on the sensed atrial rate, and in determining such rate it is critically important that neither R-waves nor T-waves be falsely sensed as a P-wave. Such may be particularly noticeable when an A-V combipolar electrode configuration is being used because, in such configuration, P-waves, R-waves, and T-waves may be sensed as being of the same order of magnitude. This problem may be made even more difficult during a mode switch, e.g., when switching a pacemaker from a DDD mode to a VVI or DDI mode, because such a mode switch tends to introduce retrograde P-waves, of which occurrences may be sensed and falsely assumed to be an antegrade P-wave.

While it is well known that various blanking schemes may be used to block or blank out unwanted T-waves and retrograde P-waves by using different blanking intervals (i.e., PVARP, automatic PVARP extension, PVAB, etc.), and thereby prevent such T-waves or retrograde P-waves from being falsely sensed as P-waves, such blanking schemes (based solely on timing considerations) have proven less than satisfactory because legitimate (antegrade) P-waves (which need to be sensed) may and do occur during these blanking intervals.

Differentiation schemes based on the morphology of the sensed waveform have also been used. Such schemes are premised on the fact that P-waves, R-waves and T-waves have inherently different shapes. Thus, in theory, all one needs to do is to examine the morphology of the sensed waveform. Unfortunately, morphology-based schemes require that the entire waveform be captured and analyzed—a process that not only requires waiting until the entire waveform has occurred, but also may require significant on-chip processing capability and processing time.

Thus, it is seen that there is a need in the implantable cardiac stimulator art to accurately detect and discriminate between P-waves, R-waves, and T-waves, without relying solely on blanking considerations or morphology. This need is particularly acute when sensing between intra-chamber electrodes, e.g., when sensing using an A-V combipolar electrode configuration.

SUMMARY OF THE INVENTION

The disadvantages and limitations of the background art discussed above are overcome by the present invention. The present invention contemplates a system and method for automatically determining the sensitivity setting for a sense amplifier by determining the threshold for sensing of undesired signals (e.g., T-waves, far-field R-waves, etc.).

Broadly, the sensing threshold for the undesired signal may be achieved either by directly measuring the peak amplitude of the undesired signal (e.g., using an A/D converter or a peak detect circuit), or by indirectly measuring the peak by detecting the presence and then the absence of the undesired signal. In order to detect the undesired signal, the present invention analyzes the time-relationship between the two or more cardiac signals.

More specifically, in one embodiment used within the ventricular channel, the sensing level for detecting an R-wave and for discriminating against T-waves may be determined by setting an adjustable sensitivity (i.e., as determined by the threshold and gain settings) of a programmable gain sense amplifier to its highest setting (e.g., its highest gain and lowest threshold settings) so that double sensing of the R-wave and the T-wave occurs. Then, the sensitivity may be incrementally decreased until only single sensing of the R-wave occurs.

An adequate safety margin is preferably added to the sensitivity setting to avoid beat-to-beat variability of the T-wave, and such sensitivity setting is thereafter used to ensure that only single sensing occurs, i.e., to ensure that only the R-wave and not the T-wave is sensed.

In a variation of the above embodiment, the system could continue adjusting the sensitivity setting to determine the peak R-wave. The system preferable includes also adding a safety margin below the peak R-wave to avoid beat-to-beat variability of the R-wave. The system may also store the amplitude and the time-relationship between the peak R-wave and the peak T-wave for statistical analysis.

In another embodiment used within the atrial channel, the sensing level for detecting P-waves and for discriminating against far-field R-waves and T-waves may be determined by setting an adjustable sensitivity setting of a programmable gain sense amplifier to its highest sensitivity setting so that triple sensing occurs, i.e., P-waves, R-waves and the T-waves are sensed simultaneously. Then, the sensitivity setting may be incrementally decreased until only single sensing of the P-waves occur. The processor then characterizes and stores the time-relationship and amplitude of each signal as each peak is detected so that proper classification of the cardiac signals can occur.

An adequate safety margin is then added to the atrial sensitivity setting, similar to that described above for R-wave sensing, and such atrial sensitivity setting is thereafter used to ensure that only single sensing occurs.

While it may appear that above embodiment presumes that the far-field R-wave and T-wave are smaller than the P-waves, even if this were not true, the processor can easily determine which signals correspond to P-waves by examining the time-relationship of each peak.

Such is the case when the present invention is used with an A-V combipolar electrode configuration, wherein R-waves are generally larger than P-waves and T-waves, but T-waves may at times be larger, the same, or smaller than P-waves. The processor simply characterizes and stores the time-relationship and amplitude of each signal as each peak is detected. After analyzing the time-relationship, the system can identify which peak corresponds to the P-wave and then add an adequate safety margin to it.

Thus, even if the patient is in complete heart block (where there is total disassociation between P-waves and R-waves), the system can reliably detect P-waves since the time-relationship between R-waves and T-waves is, physiologically, fixed. That is, the P-waves may have a variable time-relationship with respect to the R-wave, but the T-wave will always be coupled to the R-wave and fall within an expected interval. Likewise, in the instance where current of injury T-waves are larger than R-waves, the system can reliably detect R-waves based on their time-relationship.

In any of the above-described embodiments, an A/D converter or peak detector may be used to directly measure the peak cardiac signal and classify the cardiac signals as P-waves, R-waves, and T-waves based on their time-relationship and amplitude.

In yet another embodiment, the present invention differentiates P-waves, R-waves and T-waves by analyzing amplitude, duration and time-relationship for each. That is, the analysis includes measuring the amplitude and duration of a sensed signal, determining if the amplitude and duration qualify these signals as being legitimate, and then ascertaining whether the measured signal is a P-wave, R-wave or T-wave as a function of the time-relationship and amplitude within the cardiac cycle during which the peak amplitude occurs.

In yet another embodiment, the system may store a histogram of the frequency of cardiac signals having a particular time-relationship and amplitude. Thus, not only are intrinsic signals (R-waves, P-waves, and T-waves) mapped into the histogram, but paced signals and far-field signals can be separately characterized and have, effectively, their own signature. Premature beats can either be ignored or likewise characterized.

The present invention further contemplates a robust method for statistically analyzing the time-relationship and classification of P-waves, R-waves and T-waves and thereafter adjusting the sensitivity based on such classification and amplitudes.

BRIEF DESCRIPTION OF THE DRAWINGS

The above and further features, advantages and benefits of the present invention will be apparent upon consideration of the following detailed description, taken in conjunction with the accompanying drawings, in which like reference characters refer to like parts throughout, and in which.

DETAILED DESCRIPTION OF THE INVENTION

Before describing the present invention in detail, it would be helpful to first have an understanding of typical amplitude and time-relationship of the various cardiac signals.

Figure 1:
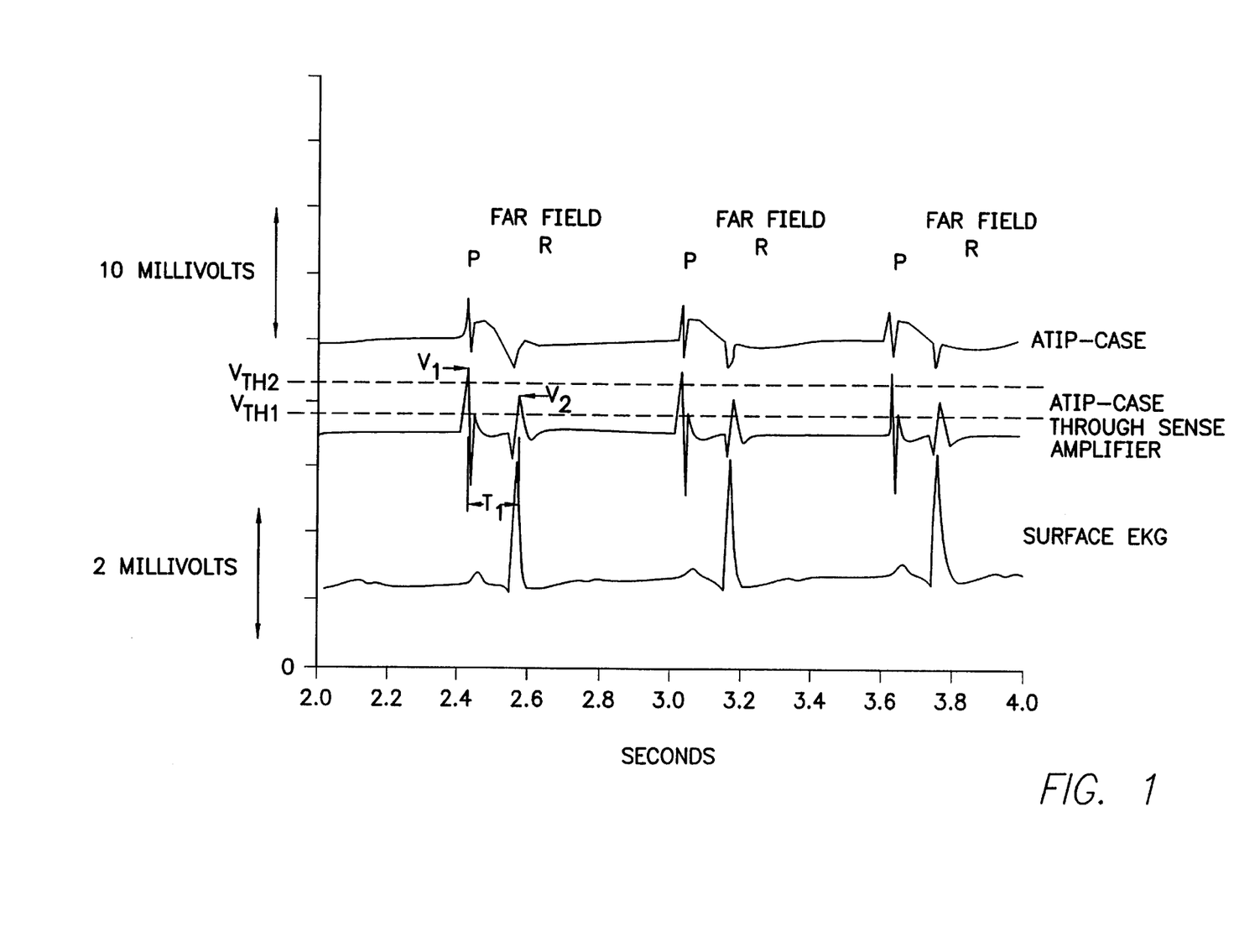
FIG. 1 is a recording of cardiac signals illustrating a first embodiment for automatically sensing P-waves using an atrial unipolar (Atip-Case) configuration.

FIG. 1 illustrates a simultaneous recording of intrinsic atrial cardiac signals. The top trace is a recording of the intracardiac signals as seen using atrial unipolar (Atip-Case) electrodes. The middle trace is a recording of the same signals at the output of an atrial sense amplifier. As a reference, the bottom trace is a surface electrocardiogram (ECG). As observed in the top and middle traces, the far-field R-wave is small compared to the near-field P-wave, and the T-wave is virtually non-existent.

As illustrated in the middle trace, if the atrial sensitivity was set to a threshold $V_{TH1}$, double sensing would occur corresponding to the P-wave and the R-wave with a coupling interval of $T_1$ (corresponding to the AV interval). It can also be seen that there is a threshold (e.g., $V_{TH2}$) within a range of thresholds below the peak P-wave and above the peak far-field R-wave which can be used for ensuring reliable detection of the P-wave without detecting the far-field R-wave.

Even if the opposite amplitude relationship were true (i.e., that P-waves were smaller than far-field R-waves), the present invention would look at the relative timing to determine whether or not conduction exists.

If conduction exists, the present invention would classify the first waveform as a P-wave, and the second waveform as the far-field R-wave and set up a blanking window at the appropriate interval (e.g., about $T_1$) so that far-field sensing would be avoided.

If, on the other hand, the patient had complete heart block, then both the amplitude and the rate for each signal would be analyzed. R-waves would be distinguished by their lower idio-ventricular rate.

Figure 2:
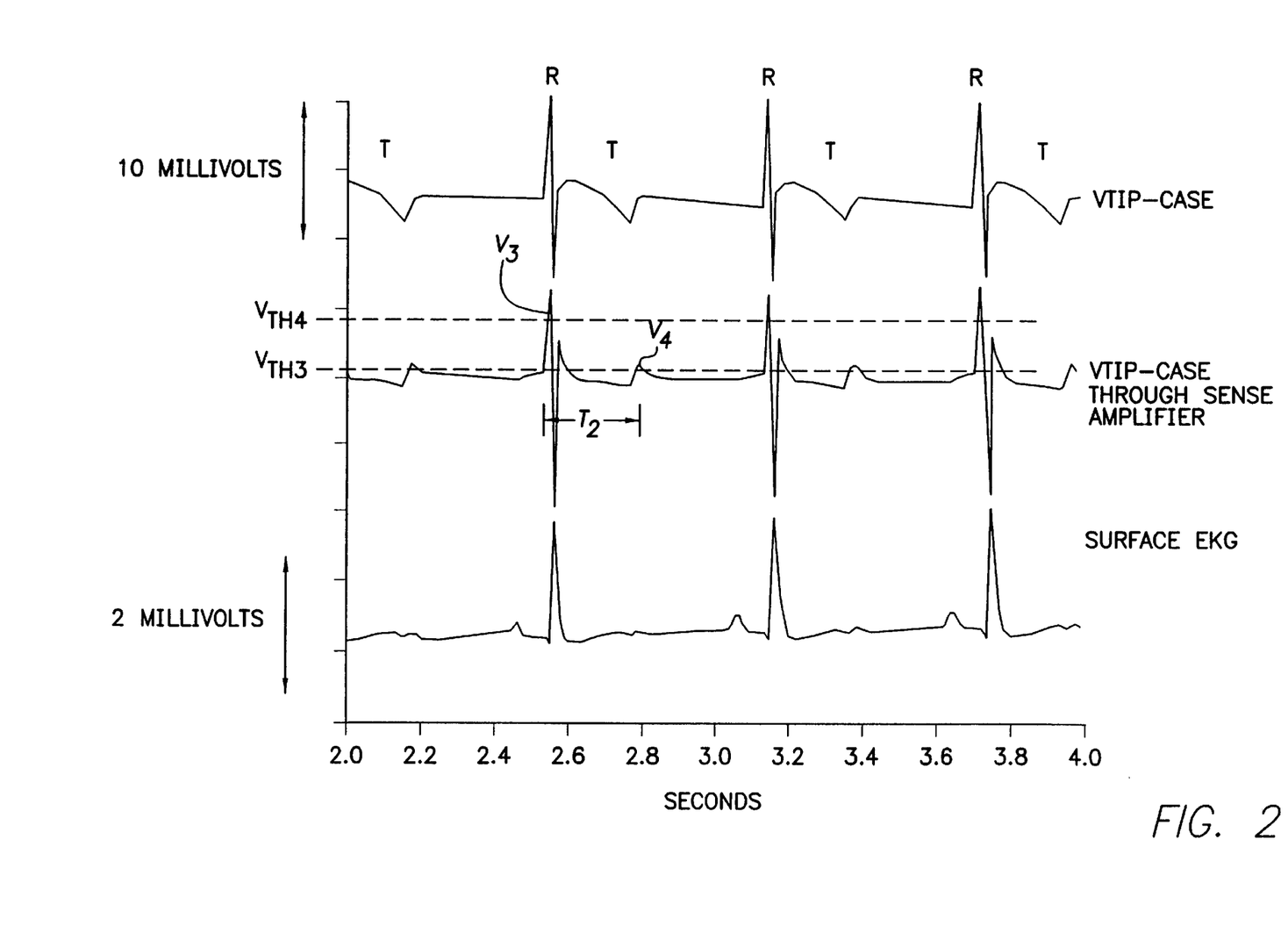
FIG. 2 is a recording of cardiac signals illustrating a second embodiment for automatically sensing R-waves using a ventricular unipolar (Vtip-Case) configuration.

FIG. 2 illustrates a simultaneous recording of intrinsic ventricular cardiac signals. The top trace is a recording of the intracardiac signals as seen using ventricular unipolar (Vtip-Case) electrodes. The middle trace is a recording of the same signals at the output of a ventricular sense amplifier. As a reference, the bottom trace is a surface electrocardiogram (ECG). As observed in the top and middle traces, the far-field P-wave is small compared to the near-field R-wave and T-wave.

As illustrated in the middle trace of FIG. 2, if the ventricular sensitivity was set to a threshold $V_{TH3}$, double sensing would occur corresponding to the R-wave and the T-wave with a coupling interval of $T_2$. It can also be seen that there is a threshold (e.g., $V_{TH4}$) within a range of thresholds below the peak R-wave and above the peak T-wave which can be used for ensuring reliable detection of the R-wave without detecting the T-wave.

The present invention determines $V_{TH4}$ by first forcing double sensing to occur by initially setting a high sensitivity (e.g., a low threshold and a high gain setting), and then adjusting the sensitivity setting until single sensing occurs and then adding an appropriate safety margin. An advantage of the present invention is that the coupling interval to the T-wave, $T_2$, is also characterized and can be used to simplify other algorithms (such as the automatic determination of post-ventricular atrial refractory period (PVARP) and post-ventricular atrial blanking (PVAB), etc.), as well as, aid in identifying current of injury (high amplitude) T-waves should they occur.

Figure 3:
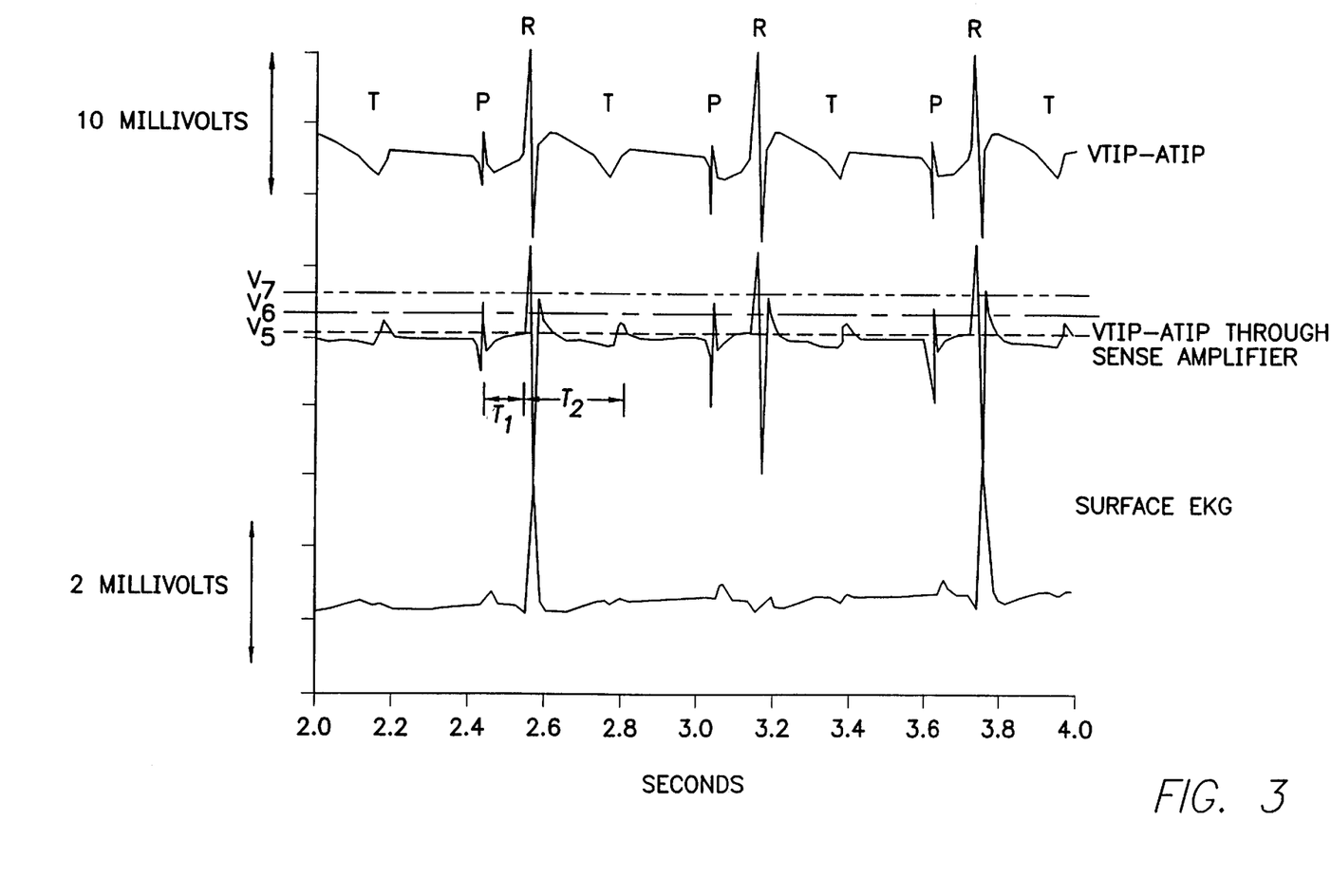
FIG. 3 is a recording of cardiac signals illustrating a third embodiment for automatically sensing P-waves and R-waves using an A-V combipolar (Atip-Vtip) configuration.

As illustrated in FIG. 3, the top trace is a recording of the intracardiac signals using A-V combipolar (Vtip-Atip) electrodes. The middle trace is a recording of the same signals at the output of a sense amplifier. For reference, the bottom trace is a surface electrocardiogram (ECG). As observed in the top and middle traces, all signals are near-field (and large). That is, the P-waves are similar in amplitude to the Atip-Case (FIG. 1) configuration; and the R-waves and T-waves are similar in amplitude to the Vtip-Case (FIG. 2) configuration.

As illustrated in the middle trace, if the sensitivity was set to a threshold $V_{TH5}$, triple sensing would occur corresponding to the P-wave, the R-wave and the T-wave with a coupling interval of $T_1$ and $T_2$ (corresponding to the AV interval and the R-wave to T-wave interval, respectively). It can also be seen that there is a threshold (e.g., $V_{TH6}$) within a range of thresholds above the peak T-wave and below the peak R-wave where double sensing would occur corresponding to the P-wave and the R-wave. And finally, there is a threshold (e.g., $V_{TH7}$) within a range of thresholds above the peak P-wave and below the peak R-wave where single sensing would occur corresponding to the R-wave.

Accordingly, ventricular sensing may be achieved by configuring a ventricular sense amplifier to detect cardiac signals at $V_{TH7}$ and atrial sensing may be achieved by configuring an atrial sense amplifier to detect cardiac signals at $V_{TH6}$. Additionally, blanking, or checking the ventricular amplifier for simultaneous sensing of R-waves, may be employed on the atrial sense amplifier to prevent the sensing of the R-waves.

Preferably, safety margins for the ventricular sense amplifier would be determined above the peak T-wave and below the peak R-wave so that beat-to-beat variations in the R-wave and T-waves would not incur loss of sensing. Likewise, safety margins for the atrial sense amplifier would be determined above the peak T-wave and below the peak P-wave so that P-waves could be discerned over the T-waves, taking into account beat-to-beat variations in the P-waves and T-waves.

Even if the amplitude relationship shown in FIG. 3 were not true (i.e., even if T-waves were larger than R-waves), the present invention would look at the relative timing and presume that the R-waves preceded the T-waves within an expected range, that P-waves generally precede R-waves within an expected range (when conduction exists) and/or that P-waves may have a variable time-relationship (when complete heart block exists). Once the system classifies each signal, it can then automatically set up a blanking windows at the appropriate interval so that appropriate sensing for P-waves and R-waves are achieved.

Figure 4:
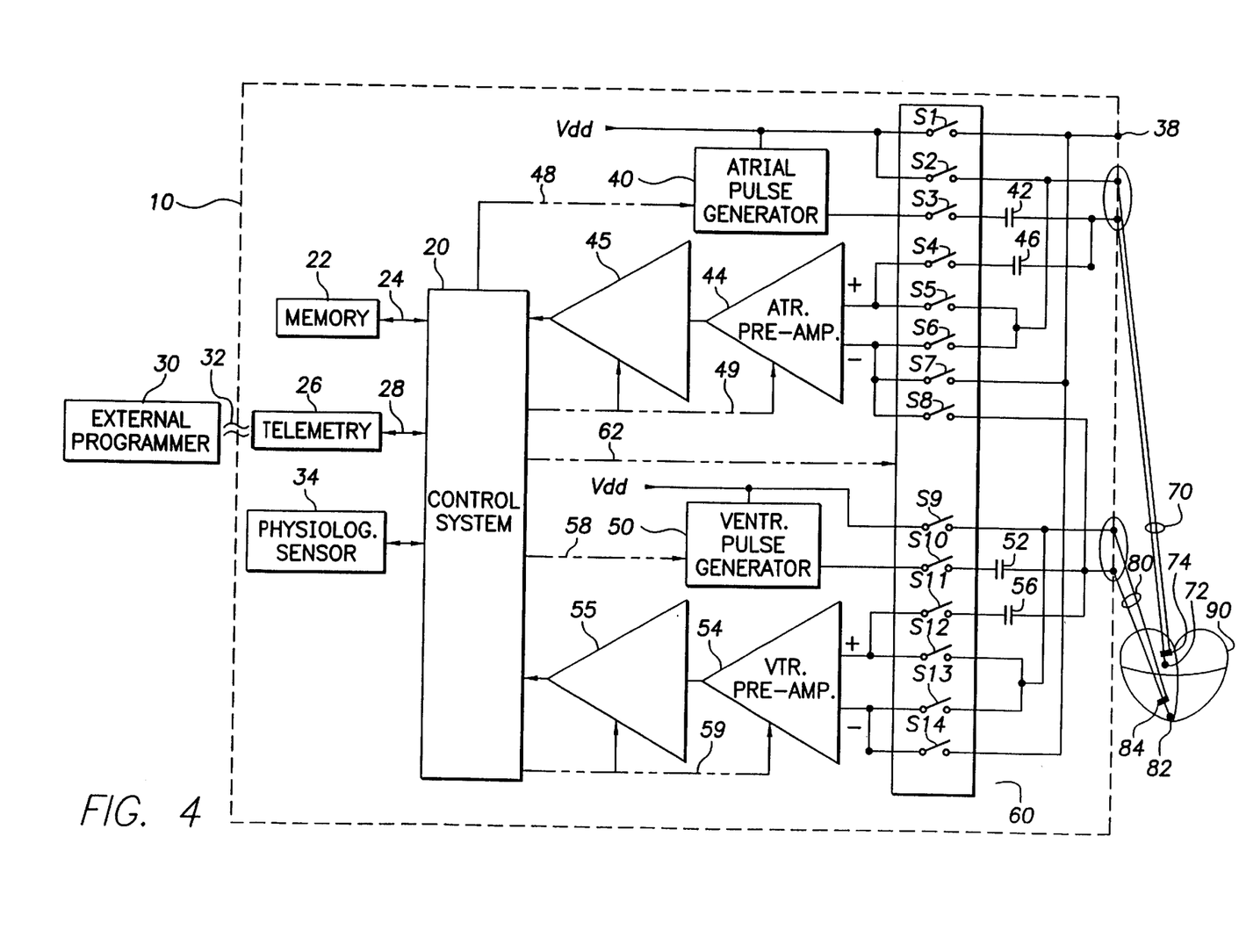
FIG. 4 is a functional block diagram of one embodiment of the invention which enables all combinations of programmable polarity.

In FIG. 4, a block diagram is shown of the preferred embodiment of an automatic sensitivity adjustment system in a dual-chambered implantable stimulation device 10.

As shown in FIG. 4, an implantable stimulation device 10 is illustrated coupled to a patient's heart 70 by way of leads 70 and 80 located in the atrium and the ventricle, respectively. The leads 70 and 80 are shown as bipolar leads for complete programmability. The atrial lead 70 includes an atrial tip electrode 72 and an atrial ring electrode 74. The ventricular lead 80 includes a ventricular tip electrode 82 and a ventricular ring electrode 84.

At the center of the stimulation device 10 is a control system 20. As is well known in the art, the control system 20 could be constructed from dedicated logic and timing circuitry, state machine circuitry, or a microprocessor.

The control system 20 is connected to a memory circuit 22 by a suitable data/address bus 24. This memory circuit 22 allows certain control parameters, used by the control system 20 in controlling the operation of the stimulation device 10, to be programmably stored and modified, as required, in order to customize the operation of the stimulation device 10 to suit the needs of a particular patient. Further, data sensed during the operation of the stimulation device 10 may be stored in the memory circuit 22 for later retrieval and analysis.

A telemetry circuit 26 is further included in the stimulation device 10. This telemetry circuit 26 is connected to the control system 20 by way of a suitable command/data bus 28. In turn, the telemetry circuit 26 may be selectively coupled to an external programming device 30 by means of an appropriate communication link 32, which may be any suitable electromagnetic link, such as an RF link. Advantageously, through the external programmer 30 and the communication link 32, desired commands may be sent to the control system 20 and stored data may be remotely received from the stimulation device 10. In this manner, non-invasive communications may be established with the implantable stimulation device 10 from a remote location.

The stimulation device 10 may include a physiologic sensor 34 to detect the exercise state of the patient, to which the control system 20 responds by adjusting the stimulation rate, but this feature is not salient to the present invention.

For generating stimulation pulses to the appropriate chamber of the heart, the control system 20 further controls an atrial pulse generator 40 and a ventricular pulse generator 50. The pulse generators 40 and 50 are coupled to a battery (not shown) which charges a respective output capacitor 42 and 52 to a desired, or programmed, value. The control system 20 generates trigger signals to the pulse generators 40 and 50 over signal lines 48 and 58, respectively, to control both the rate and the inhibition of the stimulation pulses.

A switch bank 60 receives a control signal 62 from the control system 20 which enables the appropriate combination of switches, S1–S14, to turn ON or OFF.

More specifically with respect the generating stimulation pulses, the switch bank 60 determines the polarity of the stimulation pulses (e.g., unipolar or bipolar) by selectively closing the appropriate stimulation switches for the case electrode (S1), the atrial ring electrode (S2), the atrial tip electrode (S3), the ventricular ring electrode (S9), the ventricular tip electrode (S10), as is known in the art.

The physician may also program the polarity of the pre-amplifiers 44 and 54, independent of the stimulation polarity. For example, for atrial sensing, the control system 20 would close switches in S4 and S6 for bipolar sensing; switches S4 and S7 for unipolar sensing; switches S5 and S7 for unipolar-ring sensing; and switches S4 and S8 for combipolar sensing. Likewise, for ventricular sensing, the control system 20 would close switches in S11 and S13 for bipolar sensing; switches S11 and S14 for unipolar sensing; switches S12 and S14 for unipolar-ring sensing. For purposes of combipolar sensing, typically the atrial sense amplifier is configured to sense between the Atip-to-Vtip (switches S4 and S8), and the ventricular channel is preferably configured to sense in a conventional unipolar mode, as described above.

The control system 20 further controls the rate at which the pulse generators 40 and 50 generate stimulation pulses, as well as keeping track of the timing of any refractory period, PVARP intervals, noise detection windows, alert intervals, etc., as is known in the art.

The control system 20 further controls atrial and ventricular sensing circuitry. In one embodiment, the present invention employs conventional sensing circuits that detect cardiac signals. As such, with reference to FIG. 4, the conventional atrial sensing circuitry includes a pre-amplifier 44 followed by a comparator 45, whereas the ventricular sensing circuitry includes a ventricular pre-amplifier 54 followed by a comparator 55. Accordingly, the pulse generators 40 and 50 will be inhibited whenever cardiac activity is sensed, in a demand fashion, by the respective sensing circuitry. The sensing circuitry 44, 45 and 54, 55 receive control signals over signal lines 49 and 59, for controlling the sensitivity (gain and threshold) and the timing of any blocking circuitry (not shown) coupled to the inputs of the pre-amplifiers 44 and 54.

In a second embodiment, the present invention could be employed using peak detectors. As such, and again with reference to FIG. 4, this peak detection embodiment includes pre-amplifiers 44 and 54, and peak detection circuitry 45 and 55, as is well known in the art. Alternately, the functions of blocks 45 and 55 may be combined into a single A/D converter that, when multiplexed, can measure the peak amplitude of the atrial and ventricular cardiac signals. Typically, the A/D converter is part of a separate sensing system for detecting intracardiac electrograms (IEGMs).

Regardless if which sensing scheme is chosen, the switch bank 60 controls the polarity of the pre-amplifiers 44 and 54 in one of four basic sensing configurations: bipolar (tip-ring), unipolar (tip-case), unipolar-ring (ring-case), and A-V combipolar sensing (Atip-Vtip). While this arrangement offers complete programmable polarity, it is used for illustration purposes and should not be considered limiting, since one of skill in the art could readily simplify this arrangement for dedicated polarity or single-chamber use.

From the above description of the hardware shown in FIG. 4, one of skill in the art could readily adapt the present invention to further utilize bipolar sensing of the intracardiac signals, corresponding to the unipolar signal traces shown in FIGS. 1 and 2. Bipolar sensing would only enhance the rejection of far-field signals and enable the algorithm to function more reliably. Accordingly, bipolar sensing is considered within the scope of the present invention.

The present invention may best be understood by first explaining the simpler embodiment of detecting the R-wave using a conventional sensing circuit (i.e., a preamplifier and comparator) and automatically determining the ventricular sensitivity setting before describing the atrial embodiment. However, it is within the spirit of the invention to modify the flow charts of FIGS. 5A, 5B, 6A and 6B, to utilize a peak detector or an A/D converter to measure the peak amplitudes of the cardiac signals.

Figure 5A:
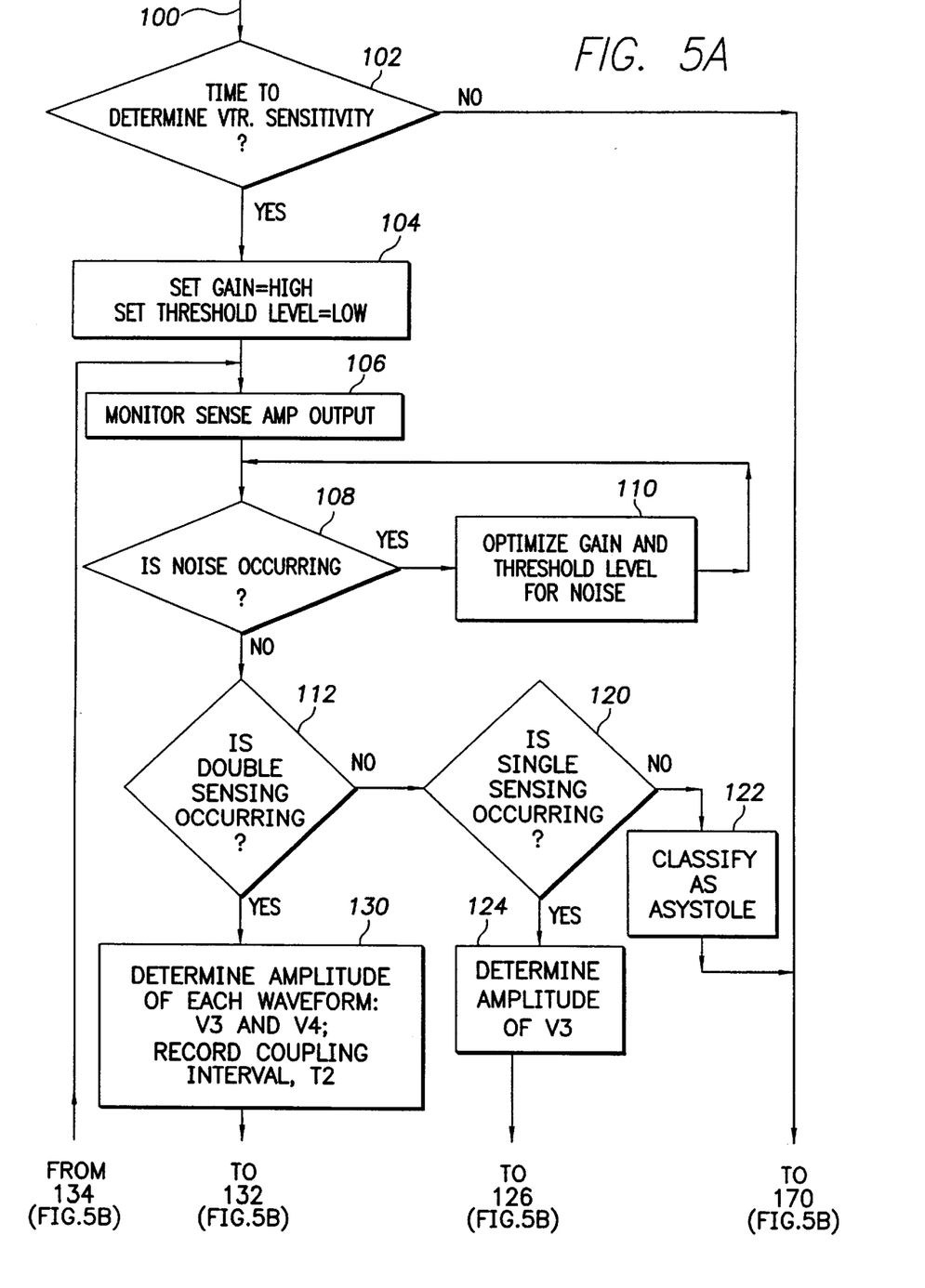
FIGS. 5A and 5B represents a flow diagram of the steps needed to implement one embodiment of the present invention, corresponding to ventricular sensitivity adjustment shown in FIG. 2.
Figure 5B:
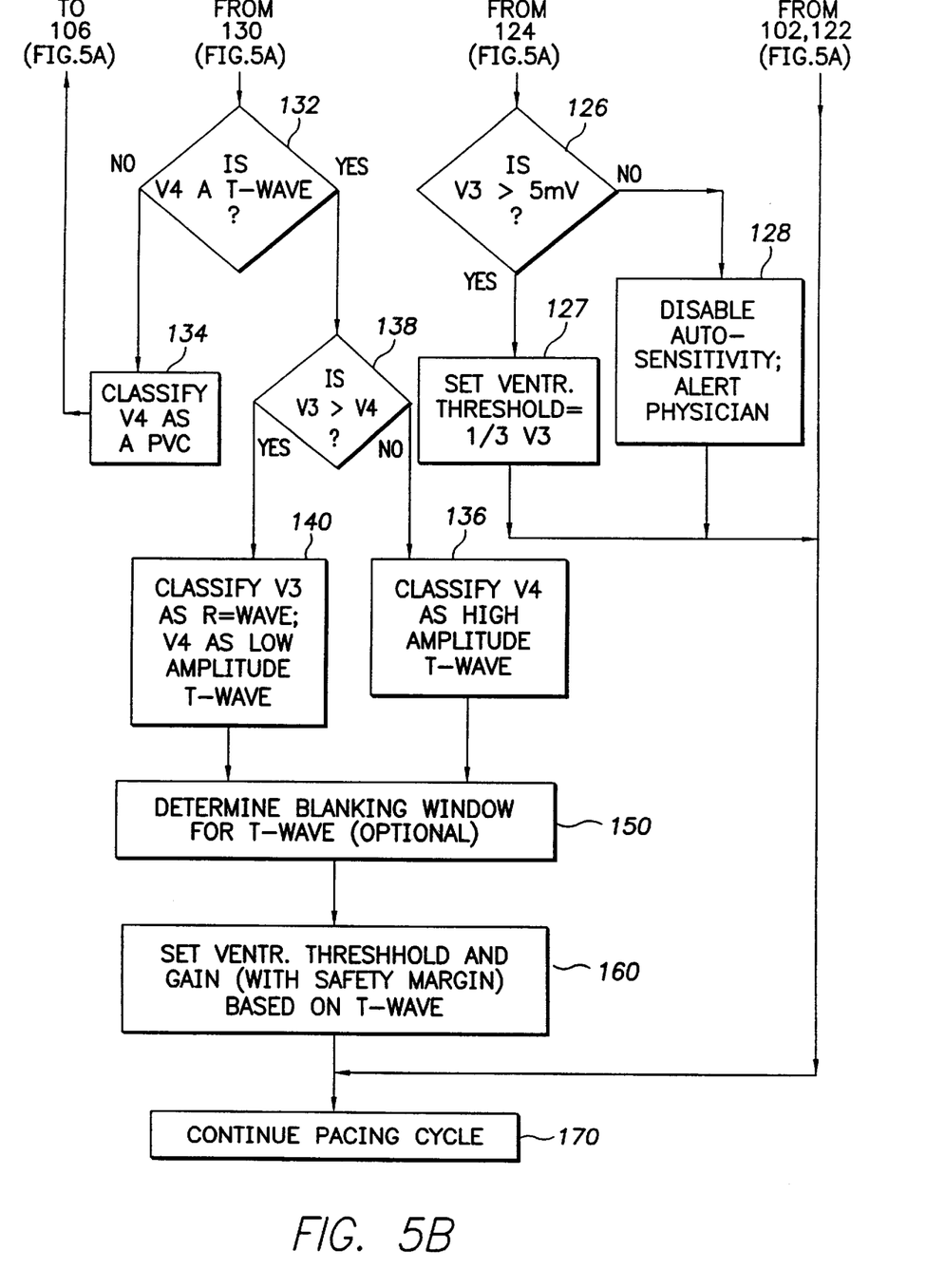

Accordingly, FIGS. 5A and 5B is a flow diagram of the steps needed to implement the second embodiment, corresponding to FIG. 2, for detecting R-waves in accordance with the present invention. As such, references to like designators and values will be used throughout the specification.

At the start (100), the invention checks to see if it is time to determine the ventricular sensitivity (block 102). This periodic check may occur routinely once a day, after a defibrillation shock, after a detected change in the rhythm, after an extended period of time without a detected cardiac signal, or after a change in the sensing electrode configuration, etc.

If it is time to test the sensitivity, then the sensitivity (i.e., gain and/or the threshold) is set so as to incur double sensing (block 104). The control system 20 will then monitor the output of the ventricular sensing circuitry 54, 55 (block 106). If it is determined that noise is occurring (block 108), then the control system 20 will attempt to optimize the gain and threshold level for noise, either by monitoring a noise window, or performing statistical analysis, as discussed in more detail below in conjunction with FIG. 7.

Once noise has been ruled out, the control system 20 determines if double sensing is occurring (block 112). If yes, then the control system 20 preferably determines the amplitude of each waveform having the values, $V_3$ and $V_4$ (FIG. 2), and the coupling interval, $T_2$ (FIG. 2).

The control system 20 may perform a variety of tests to determine if the second waveform, $V_4$, is a true T-wave (block 132), for example, by checking to see if the time interval, $T_2$, is between 200–400 ms as would be expected. More sophisticated checking could include a statistical analysis to verify that the relationship is indeed intrinsic in nature (i.e., a true T-wave will have very little variability), as also discussed in more detail below in conjunction with FIG. 7.

If the second waveform, $V_4$, is not a T-wave, it is classified as a premature ventricular contraction (PVC) (block 134) and the test sequence is repeated until PVC's do not occur.

If the second waveform, $V_4$, is determined to be a T-wave, the control system 20 determines if the first waveform, $V_3$, is larger than the second waveform, $V_4$ (block 138). If yes, then the first waveform, $V_3$, is classified as an R-wave and the second waveform, $V_4$, is classified as a low amplitude T-wave (block 140). The control system 20 may employ a blanking interval (block 150), or it may skip this step since the sensitivity will be set to avoid T-wave sensing and, advantageously, would permit sensing of R-waves during the normally "blanked" interval.

If the first waveform, $V_3$, is smaller than the second waveform, $V_4$ (block 138), then the second waveform, $V_4$, is classified as a high amplitude T-wave (block 136). For this condition, a blanking window for the T-wave is preferred (block 150) since it would be difficult to discriminate between an occasional PVC or R-wave occurring in that window and a high-amplitude T-wave.

Based on the amplitudes of the T-wave and the R-wave measured in block 130, the control system 20 would then set the ventricular sensitivity threshold and gain to an appropriate level that ensures only single sensing of the R-wave, preferably including a safety margin to avoid beat-to-beat variability (bock 160).

For completeness, the flow chart shown in FIGS. 5A and 5B also explains what would happen if only single sensing occurred (block 120). The control system 20 would determine the amplitude of the single event (e.g., having a value, $V_3$) (block 124). If the amplitude was greater than a predetermined threshold (e.g., 5 mV), then the signal is considered reliable and a threshold could be set (e.g., at ⅓ $V_3$) (block 127). If the amplitude was less than the predetermined threshold (e.g., 5 mV), then the signal is considered unreliable and autosensitivity would be disabled and the clinician would be alerted at the next interrogation (block 128).

In some patients, who are asystolic or pacemaker dependent, even single sensing may not occur (block 120, 122). In these patients, autosensitivity could continue (block 170) and periodically recheck itself until intrinsic events resumed by looping back to block 102 or could be disabled and the clinician would be alerted at the next interrogation (similar to block 128).

Figure 6A:
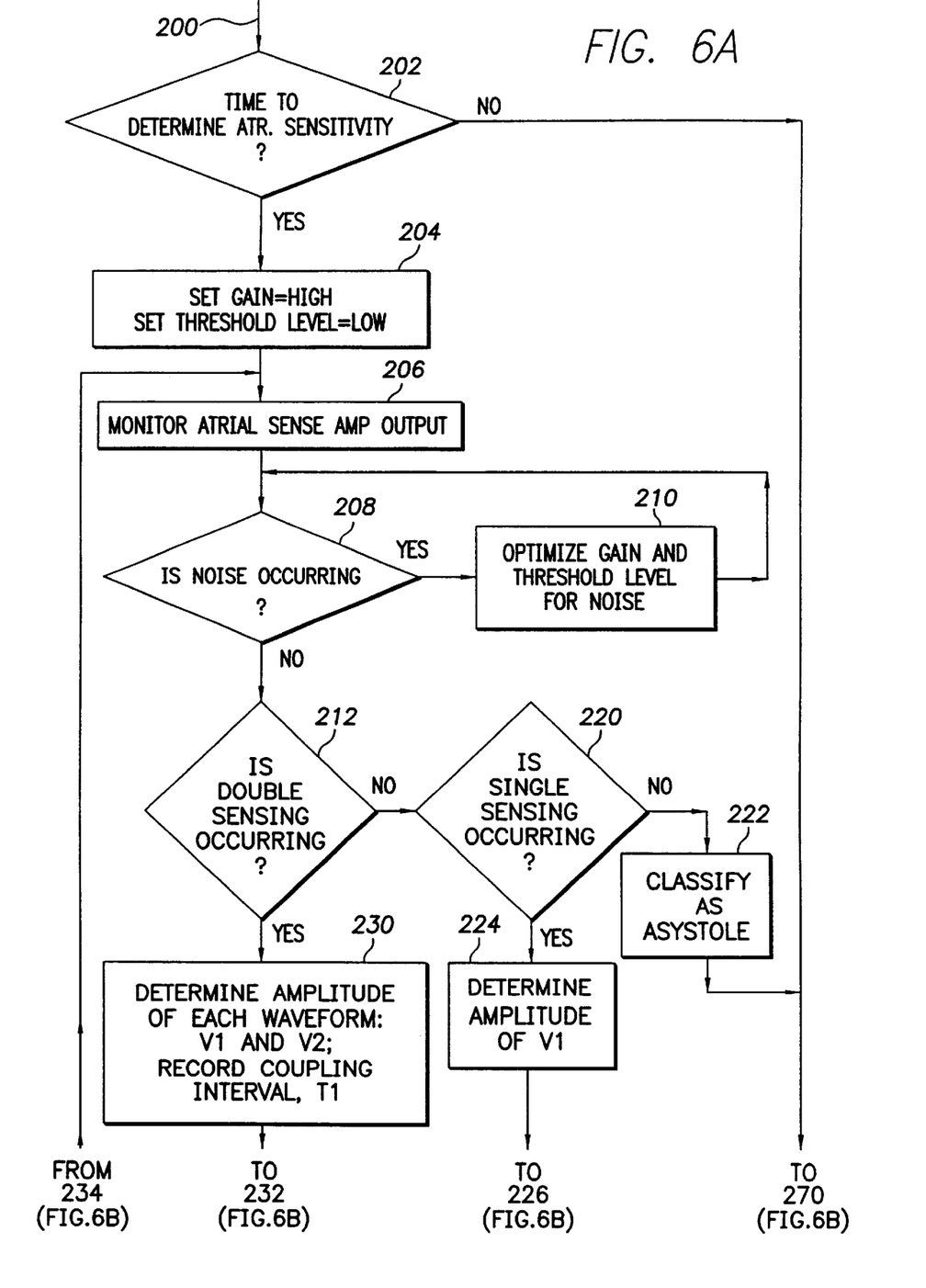
FIGS. 6A and 6B represents a flow diagram of the steps needed to implement another embodiment of the present invention, corresponding to atrial sensitivity adjustment shown in FIG. 1.
Figure 6B:
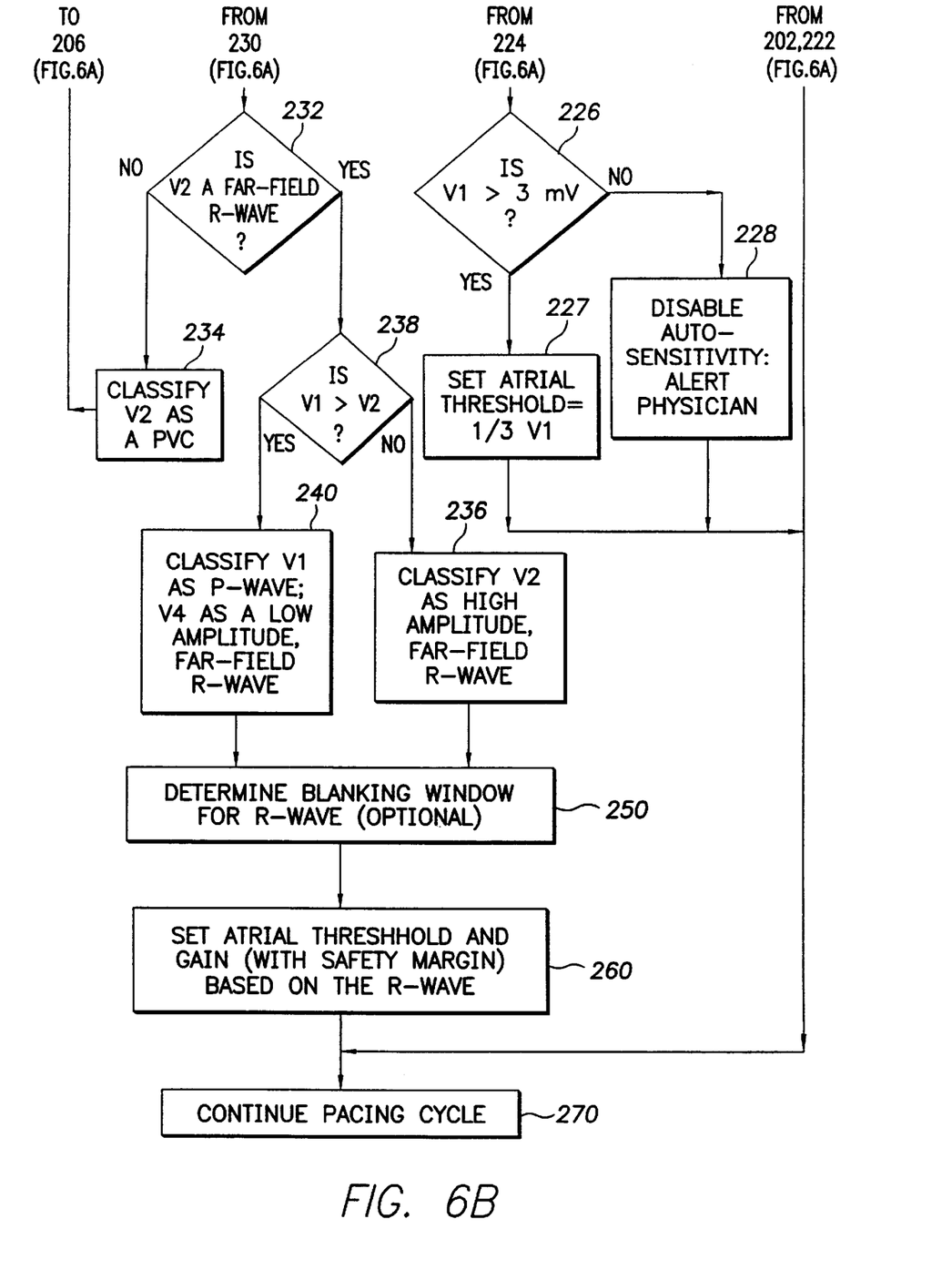

FIGS. 6A and 6B is a flow diagram of the steps needed to implement the first embodiment for detecting P-waves in accordance with the present invention. For simplicity, the flow chart in FIGS. 6A and 6B will illustrate the conditions shown in FIG. 1, with like numerals and designators used throughout.

At the start (200), the invention checks to see if it is time to determine the atrial sensitivity (block 202). This periodic check may also occur routinely once a day, after a defibrillation shock, after a detected change in the atrial rhythm, after an extended period of time without a detected cardiac signal, or after a change in sensing electrode configuration, etc.

If it is time to test the sensitivity, then the sensitivity (i.e., the gain and/or the threshold) is set so as to incur double sensing (block 204). The control system 20 will then monitor the output of the atrial sensing circuitry 44, 45 (block 206). If it is determined that noise is occurring (block 208), then the control system 20 will attempt to optimize the gain and threshold level for noise, either by monitoring a noise window, or performing statistical analysis (block 210).

Once noise has been ruled out, the control system 20 determines if double sensing is occurring (block 212). If yes, then the control system 20 preferably determines the amplitude of each waveform having a value, $V_1$ and $V_2$ (FIG. 1), and the coupling interval, $T_1$ (FIG. 1).

The control system 20 may perform a variety of tests to determine if the second waveform, $V_2$, is a conducted far-field R-wave (block 232), for example, by checking to see if the time interval, $T_1$, is between 75–250 ms as would be expected for a conducted R-wave. More sophisticated checking could include a statistical analysis to verify that the relationship is indeed intrinsic in nature (i.e., a true conducted R-wave will have very little variability in its time relationship with the P-wave).

The control system 20 may also perform a variety of tests to determine if the second waveform, $V_2$, is a non-conducted far-field R-wave (block 232). In such cases, more sophisticated testing must be performed to determine the R-wave rhythm and the P-wave rhythm. This may be achieved, in one embodiment, by comparing the amplitude and frequency of each waveform, and classifying the slower waveform as an R-wave, and the faster waveform as a P-wave, thereafter labeling the P-wave and the R-wave as $V_1$ and $V_2$ for purposes of the rest of the flow chart.

If the second waveform, $V_2$, is not an R-wave, it is classified as an ectopic beat (e.g., a PVC or a PAC)(block 234) and the test sequence is repeated until ectopic beats do not occur.

If the second waveform, $V_2$, is determined to be an R-wave ("yes" at block 232), the control system 20 determines if the first waveform, $V_1$, is larger than the second waveform, $V_2$ (block 238). If yes, then the first waveform, $V_1$, is classified as a P-wave and the second waveform, $V_4$, is classified as a low amplitude, far-field R-wave (block 240). The control system 20 may employ a blanking interval (block 250), or it may skip this step since the sensitivity will be set to avoid far-field R-wave sensing, and advantageously, would permit sensing of P-waves during the normally "blanked" interval.

If the first waveform, $V_1$, is smaller than the second waveform, $V_2$ (block 238), then the second waveform, $V_2$, is classified as a high amplitude far-field R-wave (block 236). For this condition, a blanking window for the R-wave is preferred (block 250) since it would be difficult to discriminate between an occasional PVC or R-wave occurring in that window and a true P-wave.

Based on the amplitudes of the P-wave and the R-wave measured in block 230, the control system 20 would then set the atrial sensitivity to an appropriate level that ensures only single sensing of the P-wave, preferably including a safety margin to avoid beat-to-beat variability.

For completeness, the flow chart shown in FIGS. 6A and 6B also explains what would happen if only single sensing occurred (block 220). The control system 20 would determine the amplitude of the single event (block 224). If the amplitude was greater than a predetermined threshold (e.g., 3 mV), then the signal is considered reliable and a threshold could be set (e.g., at 1 mV) (block 227). If the amplitude was less than the predetermined threshold (e.g., 3 mV), then the signal is considered unreliable and autosensitivity would be disabled and the clinician would be alerted at the next interrogation.

In some patients, who are asystolic or pacemaker dependent, even single sensing may not occur (block 222). In these patients, autosensitivity could continue (block 270) and periodically recheck itself until intrinsic events resumed by looping back to block 202 or could be disabled and the clinician would be alerted at the next interrogation (similar to block 228).

The combipolar conditions shown in FIG. 3 may be implemented by combining the flowcharts of FIGS. 5A, 5B, 6A and 6B, and adjusting the sensitivities so that initially triple sensing occurs, and decreasing the sensitivity until double sensing occurs, and finally single sensing occurs. Accordingly, the composite flowchart need not be reproduced since one of skill in the art can readily combine them. The main difference for the combipolar mode is that all signals are near-field (i.e., when sensing between an atrial electrode and a ventricular electrode, P-waves, R-waves and T-waves are all near-field and large), therefore triple sensing will most likely occur and blanking will generally be needed to block the unwanted signals. It is worth noting that the ability to triple sense aids in the classification of R-waves, since the timing between an R-wave and a T-wave is highly repeatable and occurs even in the presence of complete heart block.

In the preferred embodiment, statistics are kept on the P-wave, the R-wave and the T-wave peak amplitude such that the sensitivity of the atrial and ventricular sensing circuitry 44, 45 and 54, 55, are adjusted based on the mean value of these signals and only if the standard deviation of their respective amplitude and/or relative timing is small (indicating high repeatability and, thus, a higher probability that the waveform is not noise, atrial fibrillation or flutter, etc.).

Figure 7:
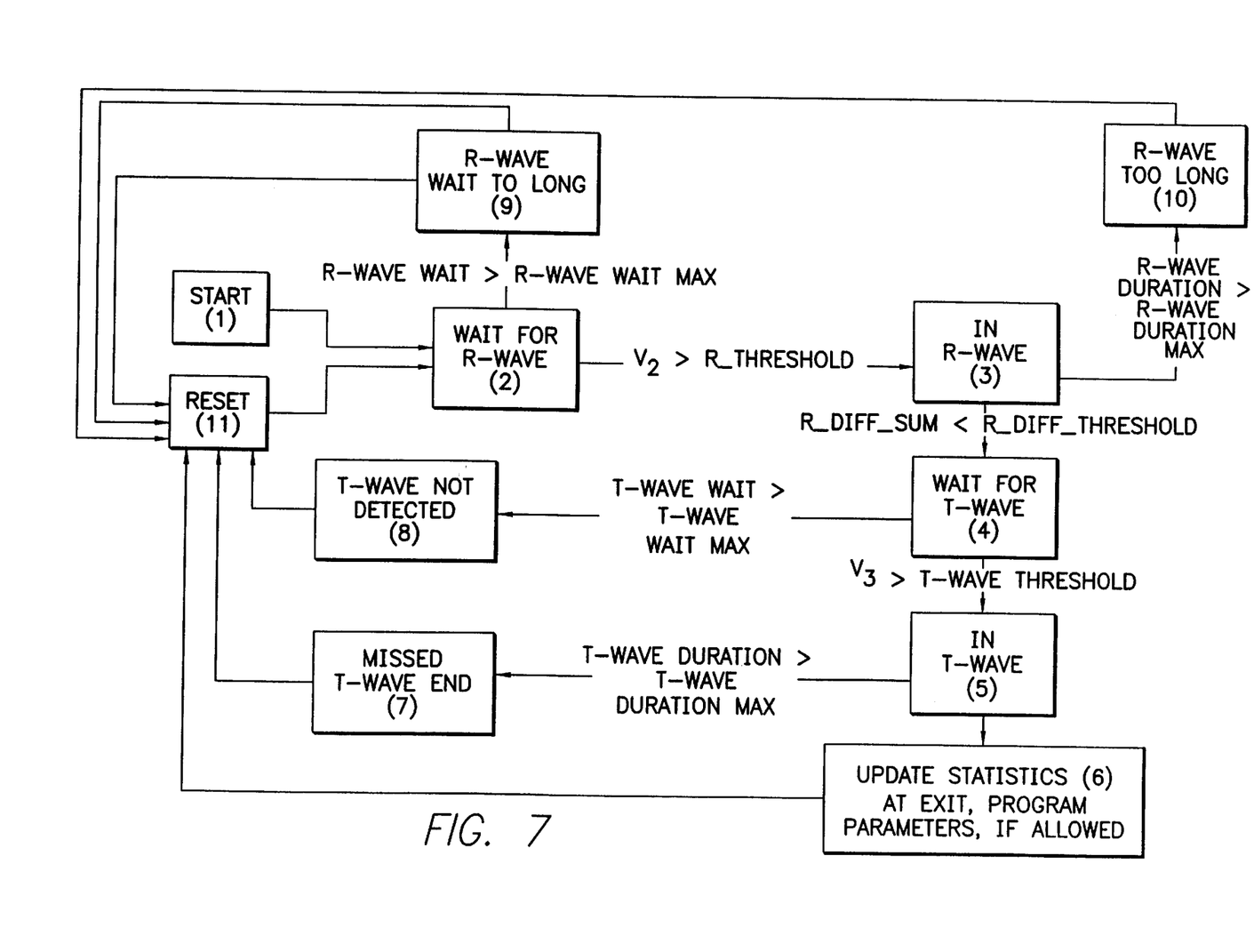
FIG. 7 represents a state diagram that provides a robust analysis of the time-relationship between the R-waves and T-waves.

The state diagram shown in FIG. 7, illustrates one implementation for classifying far-field R-waves and T-waves, as seen on the atrial sense amplifier, using statistical analysis. However, it is within the spirit of the invention to adapt the state diagram of FIG. 7 to classify near-field R-waves and T-waves, as seen on the ventricular sense amplifier, Using the atrial pre-amplifier 44, the control system 20 determines the width of the second waveform, $V_2$. It achieves this function by detecting the beginning of the far-field R-wave (using conventional techniques, such as a threshold detector), and then determining the end of the far-field R-wave by identifying a sequence of samples that are both low in amplitude and have a small derivative indicative of the baseline). In FIG. 7, this determination is achieved by states 2 and 3. Briefly, in state 2, the control system 20 waits for a second waveform having the value, $V_2$, which is greater that the predetermined threshold (e.g., R_threshold).

If a second waveform does not occur (as determined by the relationship: R-wave Wait>R-wave Wait Max), then the control shifts from state 2 to state 9 before resetting at state 11.

If the second waveform is detected (as determined by the relationship $V_2$>R_Threshold), then the minimum, maximum and peak of the R-wave are measured in state 3.

If the second waveform is too wide (R-wave Duration>R-wave Duration Max), the control shifts from state 3 to state 10 and then also resets at state 11.

If the end of the second waveform is detected, then this fiducial point is used to calculate the duration (e.g., R_Diff_Sum) of the second waveform (i.e., the far-field R-wave).

In state 4, the algorithm then determines the beginning and the end points of the T-wave, in a similar fashion (that is, by detecting a beginning threshold ($V_3$>T-wave Threshold) then by identifying a sequence of samples that are both low in amplitude and have a small derivative indicative of the baseline).

If a third waveform does not occur (as determined by the relationship: T-wave Wait>T-wave Wait Max), then the control shifts from state 4 to state 8 (T-Wave not detected) before resetting at state 11.

If the third waveform is too wide (T-wave Duration>T-wave Duration Max), the control shifts from state 5 to state 7 and then also resets at state 11.

If the beginning and end of the third waveform is detected in state 5, then these two fiducial points are used to calculate the duration (e.g., T_Diff_Sum) of the waveform, $V_3$ (i.e., the far-field T-wave). The minimum, maximum and peak of the T-wave are then measured.

From state 5, the control shifts to state 6 wherein the statistics are updated. Means and standard deviation of each of these measurements (i.e., R-wave and T-wave amplitude, including minimum, maximum and/or peak values, R-wave and T-wave duration and their spatial relationship, and the time-relationship of paced ventricular events to far-field signals). These parameters may be used to determine if the waveforms are stable before attempting to set the atrial sensitivity. Instability of any far-field R-wave, the time between a ventricular event (paced or sensed) to a corresponding far-field R-wave event or T-wave peak, will prevent reprogramming of the atrial sensitivity. Requiring that the entire far-field sequence (beginning of the R-wave, ending of the R-wave, beginning of the T-wave, and the ending of the T-wave) to be detected and consistent with earlier measurements makes the algorithm robust. Equally important, if any errors occur in states 7, 8, 9, or 10, then reprogramming of the atrial sensitivity does not occur nor does the updating of the signal statistics. Preferably, a predetermined number of error-free measurements is required before the algorithm can program the atrial sensitivity. Separate measurements and statistics are kept for paced and sensed ventricular events (dues to a latency in the measurement of each).

The steps performed by the state diagram shown in FIG. 7 ensures a high confidence that the histograms will reliably report true cardiac events and not noise, atrial fibrillation or atrial flutter.

It will therefore be perceived that the advantages of the present invention result in a system and method for automatically adjusting sensitivity in an implantable stimulation device while providing a highly desirable enhancement to implantable cardiac pacemaker therapy.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. In an implantable cardiac stimulation device, a system for Automatically adjusting sensitivity, comprising:
   a sensing circuit configured to sense first and second cardiac signals, the sensing circuit having programmable sensitivity settings;
   a pulse generator configured to generate stimulation pulses in the absence of the first cardiac signal;
   a control system, coupled to the sensing circuit and the pulse generator, programmed to automatically determine an appropriate sensitivity setting for sensing the first cardiac signal based on the sensing of the second cardiac signal.

2. The system of claim 1, wherein the control system further comprises:
   means for determining a sensing threshold for detecting the second cardiac signal; and
   means for selectively adjusting the sensing circuit to a sensitivity setting greater than the sensing threshold of the second cardiac signal.

3. The system of claim 1, wherein:
   the sensing circuit includes a comparator configured to simultaneously detect the first and second cardiac signals whenever the sensitivity is equal to or below a first value, the first value corresponding to the peak amplitude of the second signal, and further configured to single detect the first cardiac signal when the sensitivity is adjusted above the first value; and
   the control system is programmed to determine an appropriate setting for the sensing circuit above the first value.

4. The system of claim 1, wherein:
   the sensing circuit includes an A/D converter configured to measure a first and a second amplitude corresponding to the first and second cardiac signals, respectively; and
   the control system is programmed to determine an appropriate sensitivity setting based on the measured amplitude of the second cardiac signal.

5. The system of claim 1, wherein the control system comprises:
   control means for adjusting the sensitivity setting between a first and a second sensitivity setting, the first sensitivity setting corresponding to a peak amplitude of the first cardiac signal, and the second sensitivity setting corresponding to a peak amplitude of the second cardiac signal; and
   sensitivity setting means for setting the sensitivity setting to a value between the first and second sensitivity setting so that the second cardiac signal will not be sensed.

6. The system of claim 1, wherein:
   the sensing circuit comprises a ventricular sensing circuit;
   the first and second cardiac signals include R-waves and T-waves, respectively; and
   the control system is programmed to automatically determine an appropriate ventricular sensitivity setting for sensing R-waves based on the sensed T-wave.

7. The system of claim 6, wherein the control system further comprises:
   control means for determining a first range of sensitivity settings that simultaneously detects the R-waves and the T-waves, and for determining a second range of sensitivity settings that detects the R-waves without detecting the T-waves; and
   sensitivity setting means for adjusting the ventricular sensitivity setting to a value within the second range of sensitivity settings so that T-waves will not be sensed.

8. The system of claim 1, wherein:
   the sensing circuit comprises an atrial sensing circuit;
   the first and second cardiac signals include P-waves and R-waves; and
   the control system is programmed to automatically determine an appropriate atrial sensitivity setting for sensing P-waves based on the sensed R-wave.

9. The system of claim 8, wherein the control system comprises:
   control means for determining a first range of sensitivity settings that simultaneously detects P-waves and the R-waves, and for determining a second range of sensitivity settings that detects P-waves without detecting the R-waves; and sensitivity setting means for adjusting the atrial sensitivity setting to a value within the second range of sensitivity settings so that R-waves will not be sensed.

10. The system of claim 8, wherein:
the sensing circuit is adapted to detect a third cardiac signal corresponding to T-waves; and
the control system is programmed to automatically determine an appropriate atrial sensitivity setting for sensing P-waves based on the amplitude of at least one of the sensed R-wave and the sensed T-wave.

11. The system of claim 1, wherein:
the sensing circuit includes means for measuring a first and a second amplitude corresponding to the first and second cardiac signals, respectively; and
the control system includes means for determining the time relationship between the first and second cardiac signals, and for determining an appropriate sensitivity setting based on the measured amplitude and timing of the second cardiac signal relative to the first cardiac signal.

12. The system of claim 11, wherein:
the sensing circuit comprises a ventricular sensing circuit;
the first and second cardiac signals include R-waves and T-waves;
the control system is programmed to automatically analyze both timing and amplitude relationships of the first and second waveforms to determine which waveform is an R-wave and which waveform is a T-wave, and to determine a sensitivity setting for the R-wave based on the amplitude of the T-wave.

13. The system of claim 12, wherein the control system further comprises:
means for classifying the second cardiac signal as a T-wave only when the timing between the first and the second cardiac signal is consistent within a prescribed amount.

14. The system of claim 13, wherein the control system further comprises:
means for classifying the second cardiac signal as a premature beat, and ignores such premature beats, when the timing between the first and the second cardiac signal is not consistent within a prescribed amount.

15. The system of claim 13, wherein the control system further comprises:
means for classifying the second cardiac signal as a high amplitude T-wave when the amplitude of the second waveform is greater than the first cardiac signal and the timing between the first and the second cardiac signal is consistent within a prescribed amount; and
means for blanking the sensing circuit from sensing the high amplitude T-wave.

16. The system of claim 11, wherein:
the sensing circuit comprises an atrial sensing circuit;
the first and second cardiac signals include P-waves and R-waves;
the control system is programmed to automatically analyze both timing and amplitude relationships of the first and second waveforms to determine which waveform is a P-wave and which waveform is an R-wave, and to determine a sensitivity setting for sensing the P-wave based on the amplitude of the R-wave.

17. The system of claim 16, wherein the control system further comprises:
means for classifying the second cardiac signal as an R-wave only when the timing between the first and the second cardiac signal is consistent within a prescribed amount, thereby indicating that conduction exists between the atrium and the ventricle.

18. The system of claim 16, wherein the control system further comprises:
means for detecting a first and a second amplitude pattern for a plurality of cardiac signals;
means for detecting a first timing pattern between the cardiac signals having the first amplitude pattern, and for detecting a second timing pattern between the cardiac signals having the second amplitude pattern;
means for determining which of the first and the second timing patterns is slower; and
means for classifying cardiac signals having the slower timing pattern as R-waves, and for classifying the cardiac signals having the faster timing pattern as P-waves.

19. The system of claim 18, wherein the control system further comprises:
means for determining if cardiac signals classified as R-waves are higher in amplitude than the amplitude of the cardiac signals classified as P-waves; and
means for blanking the sensing circuit from sensing the higher amplitude R-waves.

20. The system of claim 16, wherein:
the sensing circuit is adapted to detect a third cardiac signal corresponding to T-waves; and
the control system is programmed to automatically analyze both timing and amplitude relationships of the third waveform relative to the first and the second waveforms to determine which waveform is a P-wave, which waveform is an R-wave, and which waveform is a T-wave, and to determine a sensitivity setting for sensing the P-wave based on the amplitude of at least one of the sensed R-wave and the sensed T-wave.

21. The system of claim 20, wherein the control system further comprises:
means for determining the duration of each of the first, second and third cardiac signals;
means for automatically analyzing duration of the first, second and third waveforms before determining which waveform is a P-wave, which waveform is an R-wave, and which waveform is a T-wave; and
means for ignoring waveforms that have a duration greater than a prescribed amount.

22. In an implantable stimulation device having a sense amplifier configured to sense a first cardiac signal, a pulse generator configured to generate stimulation pulses in the absence of the first cardiac signal, and a control system capable of controlling the pulse generator and the sense amplifier, the sense amplifier having a plurality of programmable sensitivity settings, and a method for automatically adjusting sensitivity of the sense amplifier, comprising the steps of:
determining a sensing threshold for detecting a second cardiac signal; and
selectively programming the sense amplifier to a sensitivity setting greater than the sensing threshold of the second cardiac signal.

23. The method of claim 22, wherein the step of determining a sensing threshold for the second cardiac signal comprises the steps of:
adjusting the sensitivity setting of the sense amplifier until the threshold of double sensing occurs, corresponding to the simultaneous sensing of the first and the second cardiac signal.

24. The method of claim 22, wherein the step of determining a sensing threshold for the second cardiac signal comprises the steps of:

measuring a peak amplitude for the second cardiac signal and correlating the peak amplitude to a sensitivity threshold.

25. The method of claim 22, further comprising the steps of:

determining a sensing threshold for detecting the first cardiac signal; and selectively programming the sense amplifier to a sensitivity setting between the sensing threshold of the first and second cardiac signals.

26. The method of claim 25, further comprising the steps of:

determining a safety margin below the sensitivity threshold for the first cardiac signal and above sensitivity threshold for the second cardiac signal to thereby define an allowable range of sensitivities that will detect the first cardiac signal; and setting the sensitivity setting within the allowable range defined by the safety margin.

27. In an implantable stimulation device having a sense amplifier configured to sense a first and a second cardiac signal, a pulse generator configured to generate stimulation pulses in the absence of the first cardiac signal, a memory for storing measured data, and a control system capable of controlling the pulse generator and the sense amplifier, the sense amplifier having a plurality of programmable sensitivity settings, and a method for adjusting the sensitivity of the sense amplifier comprising the steps of:

sensing the first and second cardiac signals;

measuring amplitude, duration and a time relationship between the first and second cardiac signals;

storing statistical data for the amplitude, duration and the time relationship for the first and second cardiac signals;

comparing the current amplitude, duration and time relationship to the stored statistical data;

triggering the storage of the current amplitude, duration and time relationship only if such data is within a predetermined delta of the stored statistical data;

analyzing the stored statistical data to determine a first and a second amplitude pattern, and to determine a first timing pattern for cardiac signals having the first amplitude pattern, and to determine a second timing pattern for cardiac signals having the second amplitude pattern;

classifying the first cardiac signal as one of a P-wave or an R-wave based on the respective amplitude and time relationship patterns; and adjusting the sensitivity setting for sensing the first cardiac signal based on the amplitude of the second cardiac signal so that the second cardiac signal is not detected.

* * * * *